United States Patent [19]

Tate et al.

[11] Patent Number: 5,764,353
[45] Date of Patent: Jun. 9, 1998

[54] BACK SIDE DAMAGE MONITORING SYSTEM

[75] Inventors: Naoto Tate, Camas; Eva Brown, Vancouver; Michito Sato, Camas, all of Wash.

[73] Assignee: SEH America, Inc., Vancouver, Wash.

[21] Appl. No.: 758,423

[22] Filed: Nov. 29, 1996

[51] Int. Cl.[6] .................................................. G01N 21/00
[52] U.S. Cl. ..................................... 356/239; 356/237
[58] Field of Search ............................ 356/239, 430, 356/431, 240, 445, 237, 371, 446; 156/628, 636, 643, 645, 651, 654, 657, 662; 250/550, 562, 563, 572

[56] References Cited

U.S. PATENT DOCUMENTS

| | | | |
|---|---|---|---|
| 4,053,335 | 10/1977 | Hu | 148/174 |
| 4,141,780 | 2/1979 | Kleinknecht et al. | 156/626 |
| 4,410,395 | 10/1983 | Weaver et al. | 156/662 |
| 4,547,073 | 10/1985 | Kugimiya | 356/371 |
| 5,066,359 | 11/1991 | Chiou | 156/651 |
| 5,196,716 | 3/1993 | Moriya et al. | 250/572 |

OTHER PUBLICATIONS

Operating Manual, High Yield Technology Inc., Optical Precipitate Profiler, Division of Pacific Scientific Company, Rev. Mar., 1994, pp. 1-1 through 1-6 cover sheet.

Semiconductor Materials & Process Technology Handbook for VLSI & ULSI, Edited by Gary E. McGuire, Noyes Publications, Copyright 1988, pp. v through xiii and two cover sheets.

Silicon Processing, D.C. Gupta, Editor, ASTM STP 804, A symposium sponsored by ASTM Committee F-1 on Electronics, National Bureau of Standards, and Stanford University, San Jose, CA., 19-22 Jan. 1982, Printed in Baltimore, Md (b) Jun. 1983, pp. 5 through 23 with three cover sheets.

Preparation of Samples for Microscopic Examination #7 and Microscopy & Photocopy #8 Chapter #7 was coauthored by Stacy B. Watelski, at least as early Jan. 1, 1996, 187 through 241.

Semiconductor Measurements and Instrumentation, W.R. Runyan, Special Circuits Department, Texas Instruments Incorporated, McGraw-Hill Book Company, Copyright 1975 Editors for this book were Tyler G. Hicks, Lester Strong, & the production supervisor George Dechsner, pp. 21 through 63 with three cover sheets.

Vol. 36, Impurity Diffusion & Gettering in Silicon, Editors Richard B. Fair, Charles W. Pearce, Jack Washburn Symposium held Nov. 27-30, 1984, Boston, Mass. Copyright 1985 by Materials Research Society pp. vii, no number page, 160-174, and two cover sheets.

*Primary Examiner*—Frank G. Font
*Assistant Examiner*—Michael P. Stafira
*Attorney, Agent, or Firm*—Bell Seltzer Intellectual Property Group of Alston & Bird LLP

[57] ABSTRACT

A method of measuring and monitoring the back side and interior defect density of a wafer from its back side by substantially increasing the back side reflectivity through lapping, etching and controlled back side damage, then measuring defect density with an optical scanner.

8 Claims, 3 Drawing Sheets

BACK SIDE DAMAGE MONITORING SYSTEM

BACKGROUND OF THE INVENTION

There are numerous defects that may occur during the growth and subsequent processing of crystal-line silicon semiconductors for wafers suitable to fabricate electronic devices therefrom, chief among which may be mentioned crystallographic defects, metallic defects, oxygen precipitates, and surface particulate contamination. Some defects are undesirable at any level, some are beneficial in moderation, and some are absolutely necessary.

The different crystallographic defects that occur in such wafers can be categorized generally as local defects, aggregate defects, miscellaneous defects, shape defects (no atomic displacement), radiation defects, and surface defects. One category of surface defect of particular interest is known as stacking faults.

Stacking faults result from anomalies in the growth of succeeding crystalline layers. Stacking faults are categorized as either intrinsic or extrinsic. Intrinsic faults occur when a portion of a layer is discontinuous, as shown in FIG. 1, and extrinsic faults occur when a partial extra layer has been included, as shown in FIG. 2. One type of intrinsic fault could be caused by the collapse of a vacancy cluster, while a variety of crystal growth anomalies are responsible for both extrinsic and intrinsic faults. For example, in some regions the atoms might nucleate in an undesirable fashion or there might be a thin foreign platelet which when overlaid with crystalline layers produces a stacking fault. For faults introduced during crystal growth, the region around them usually does not deform as shown in FIG. 1, but rather the fault propagates during additional crystal growth as a differently stacked region separated by additional faults on various planes. Fault traces intersecting the surface will give stacking fault outlines.

Electronic devices such as transistors are fabricated from the so-called "active device region" of a silicon wafer which is generally the front surface region of the wafer that is free from destructive defects. If stacking faults are present in the active device region then the electronic devices fabricated therefrom may not function properly. Accordingly, techniques have been developed to control and monitor both the location and number of stacking faults in the wafer.

As to metallic impurities within wafers, gettering is used as a method of controlling such defects. Two known methods of performing gettering are intrinsic gettering and extrinsic gettering. Intrinsic gettering comprises the gathering of defects deep within the silicon wafer, thereby keeping the impurities away from the active device region of the wafer during subsequent thermal processing which occurs when fabricating electronic devices therefrom. Extrinsic gettering involves the introduction of controlled damage to the back side of a wafer, which is beneficial because it tends to prevent migration of impurities such as metallic impurities upward into the active device region during subsequent thermal treatment. There are several methods of inducing controlled back side damage to the wafer, such as by abrasive blasting, by ion implantation, by laser beam, and by direct surface abrasion.

The preferred method of inducing controlled back side damage to a silicon wafer is by abrasive sand blasting by a wet sand blasting process comprising directing a pressurized stream of abrasive material mixed with a liquid against the back side of the wafer; the result is a pitting of the back side of the wafer.

As previously indicated, during the processing of wafers undesirable impurities may be introduced. The front surface of the wafer is polished prior to the fabrication of electronic devices therefrom and the back surface is roughened by any suitable controlled back side damage technique.

Special processing is required to detect stacking faults in a wafer, because such faults are not visible to the naked eye. To cause the stacking faults to become visible (known as "activating the defects"), oxide layers are formed on the front and back surfaces of a randomly selected wafer from production by heating the same at about 1100° C. for about 1.5 hours, typically in a quartz oxidation furnace; the resulting oxidized wafer is known as a "monitor wafer." $SiO_2$ layers on those portions of the monitor wafer containing the stacking faults induce oxidation stacking faults. The $SiO_2$ layers are then selectively removed by etching, preferably using hydrofluoric acid, followed by delineation of the surfaces by preferential etching to reveal the stacking faults. Preferred etchants are chromate- and dichromate-containing solutions. A portion of each surface of the monitor wafer is then visually examined by an operator with a manually operated Nomarski-type metallurgical microscope to count the number of defects that are visible per unit area to determine whether the defect density is within tolerances.

A technique suitable for measuring defects on a wafer's front surface only utilizes a laser scanner, commercially available as an Optical Precipitate Profiler from High Yield Technology, Inc. of Sunnyvale, Calif. This instrument uses a laser beam aimed at the front side of a wafer to measure the oxygen precipitates and other defects within and on the front side surface of the wafer. However, it is generally accepted that such a laser scanner is not suitable for measuring the defects on the back side surface of the wafer or inside the wafer from its back side surface, because the back side roughness includes damage induced for extrinsic gettering tends to scatter the laser beam, which in turn generates high "noise" levels, thereby obscuring defect measurement.

The elaborate fabrication of monitor wafers and the use of a manually operated microscope to determine back side defect density have several drawbacks. For example, in addition to the oxidation time required, an expensive quartz oxidation furnace is required. The $SiO_2$ etching of the wafer requires the use of a chemical wet bench and extremely hazardous chemicals, such as hydrofluoric acid. In addition, the chemicals used for $SiO_2$ etching and preferential etching require expensive waste water treatment for proper disposal. Defects on the back side of the wafer are observable only with a manually operated microscope and even such limited observation requires an excessive amount of time.

What is desired, therefore, is an non-hazardous, automated method of determining the defect density of the back side of the wafer for efficient process control.

BRIEF SUMMARY OF THE INVENTION

The present invention overcomes the aforementioned drawbacks of the prior art by a method of monitoring the back side defect density of a wafer comprising the steps of lapping, etching, and imparting controlled damage to the back side surface of the wafer. Thereafter, an optical scanning inspection device transmits light to and through the wafer and through detection of the degree of deflection of the light from the wafer the defect density is measured.

With the method of the present invention the reflectivity of the back side surface of the wafer is sufficiently high to permit the scanner to determine defect density in the same manner it has been used in monitoring defect density on the front side of wafers, thus allowing high-speed automation of monitoring back side defect density. This improved technique eliminates the need for the special fabrication of a monitor wafer together with its attendant fabrication steps of wafer oxidation in an oxidation furnace, $SiO_2$ etching and preferential etching, which in turn eliminates the corresponding energy, safety and waste water treatment and disposal problems. In addition, the time-consuming task of visual inspection by manual use of a microscope is eliminated.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
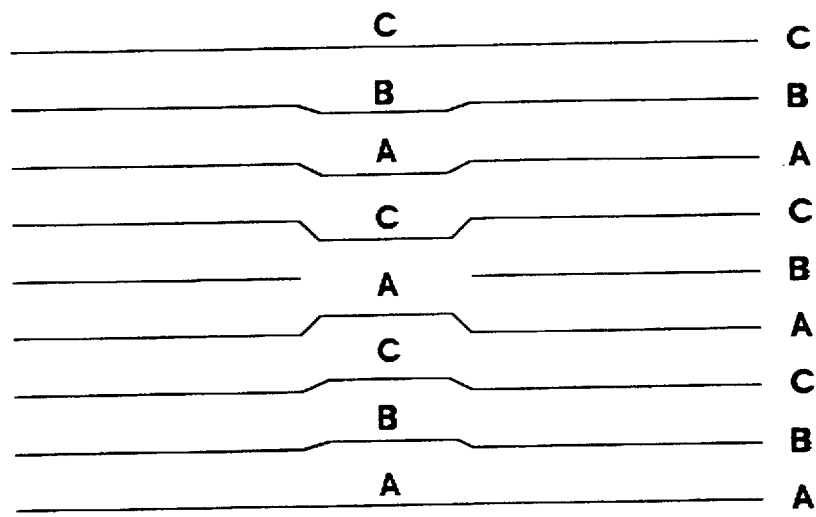
FIG. 1 is an illustration of an intrinsic stacking fault.
Figure 2:
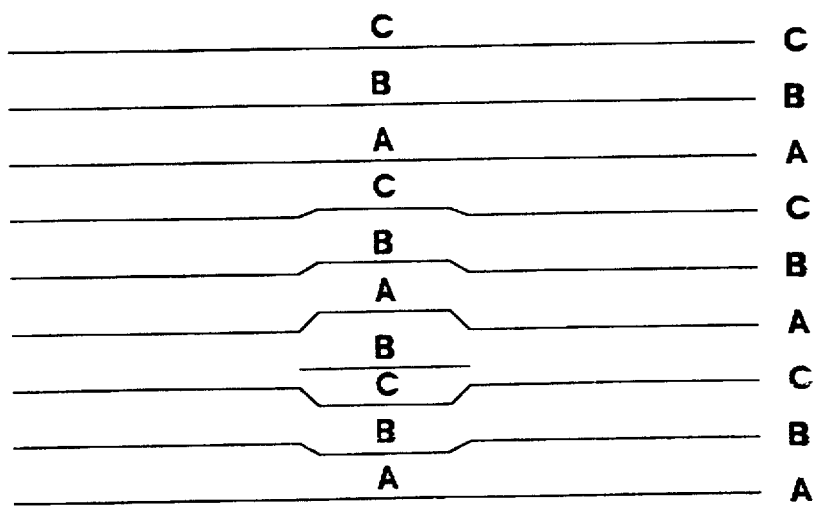
FIG. 2 is an illustration of an extrinsic stacking fault.
Figure 3:
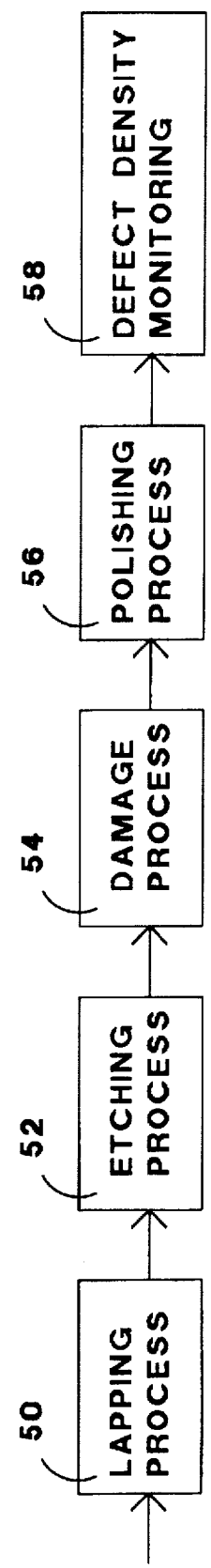
FIG. 3 is a flow chart of the process of the present invention.

Referring to FIG. 3, processing of production sliced silicon wafers generally involves using a conventional lapping process 50 to level the front and back side surfaces of a wafer, to cut the wafer down to a specified thickness, and to remove saw marks resulting from cutting the wafer from the ingot. Then a known etching process 52, typically an acidic etch, is applied to the front and back side surfaces of the wafer to remove 15–20 microns of silicon from each side in order to remove any material damaged by the lapping process and other metallic contamination resulting from the process of producing the wafer. The etching process typically uses an aqueous solution containing the acids $HNO_3$, HF, and $CH_3COOH$ in a volumetric ratio of 2:1:1, respectively. The roughness of both sides of the wafer surfaces at this point are primarily a result of the etching process 52. Thereafter, the back side surface of the wafer is subjected to a standard controlled back side damage process 54 for gettering during subsequent thermal treatment. Now the roughness of the back side surface is primarily a result of the combination of the etching process 52 and the controlled back side damage process 54. The front side surface of the wafer is then polished in a conventional manner with a polishing process 56. In order to detect stacking faults on the back side surface of the wafer with a microscope, as previously described, fabrication of a monitor wafer would be required, along with significant additional processing steps and all of their attendant drawbacks.

The inventors discovered that a laser scanner could be used to measure the stacking fault density on the back side surface of a silicon wafer if the noise levels generated by the defects caused by the etching process 52 and the controlled back side damage process 54 could be sufficiently reduced. It was further discovered that upon sufficient reduction of these noise levels, the defect density within the silicon wafer subsurface of the back side could also be measured.

A laser scanner such as the Optical Precipitate Profiler is based on Nomarski differential interference contrast microscopy to detect single defects, the defect-free zone depth and its uniformity across the entire wafer, surface particulate contamination, and polishing defects. The Profiler uses a 1.3 micron wavelength infrared laser that is partly deflected and partly scattered when it strikes a rough surface, such as the surface resulting from the etching process 52 and the damage process 54. When the degree of roughness is sufficiently high, the laser is mostly scattered, resulting in the generation of nonsensical data which may be characterized as "white noise," and which prevents measurement of defect density.

Current processing technology for a monitor wafer results in a relatively low back side surface reflectivity in the range of about 10% to 25%. To reduce the noise levels caused by such low reflectivity, the inventors have determined that the reflectivity of the back side surface needs to be substantially increased. The reflectivity of the back surface can be increased by removing more silicon than the 15–20 microns usually removed during conventional etching. However, conventional wisdom teaches that if the etching process removes more than 15–20 microns in order to increase the wafer's back side reflectivity, then the wafer will exhibit undesirable characteristics such as an orange peel effect and deterioration of surface flatness. Surprisingly, it has been discovered that if up to 50 microns of silicon is removed from each side of the wafer then the reflectivity of the back side surface, even after imparting controlled back side damage, is raised to around 90% with no orange peel effect and no significant deterioration of surface flatness. Most importantly, with such an increase in back side reflectivity, detrimental noise levels all but disappear, permitting defect density on the back side of the wafer to be directly measurable by commercially available scanner technology. In addition, such an increase in the reflectivity of the back side surface permits such measurement of defect density within the wafer's subsurface from its back side.

The preferred reflectivity of the back side for optimum use of the profiler is 95% to 100%

EXAMPLE

A batch of silicon wafers was processed by conventional steps with the exception of the acid etching step which was continued sufficiently longer than normal so as to remove 50 microns of material from each side of the wafers. The cumulative effect of the lapping, etching and controlled back side damaging steps resulted in a back side reflectivity of around 90%.

The following is a tabulation of microns of material removed (summation of both sides) versus the reflectivity (brightness) measured as a result:

| Removal (microns) | Brightness (%) |
| --- | --- |
| 10 | 10 |
| 20 | 17–18 |
| 30 | 35 |
| 40 | 55 |
| 100 | 98 |

Figure 4:
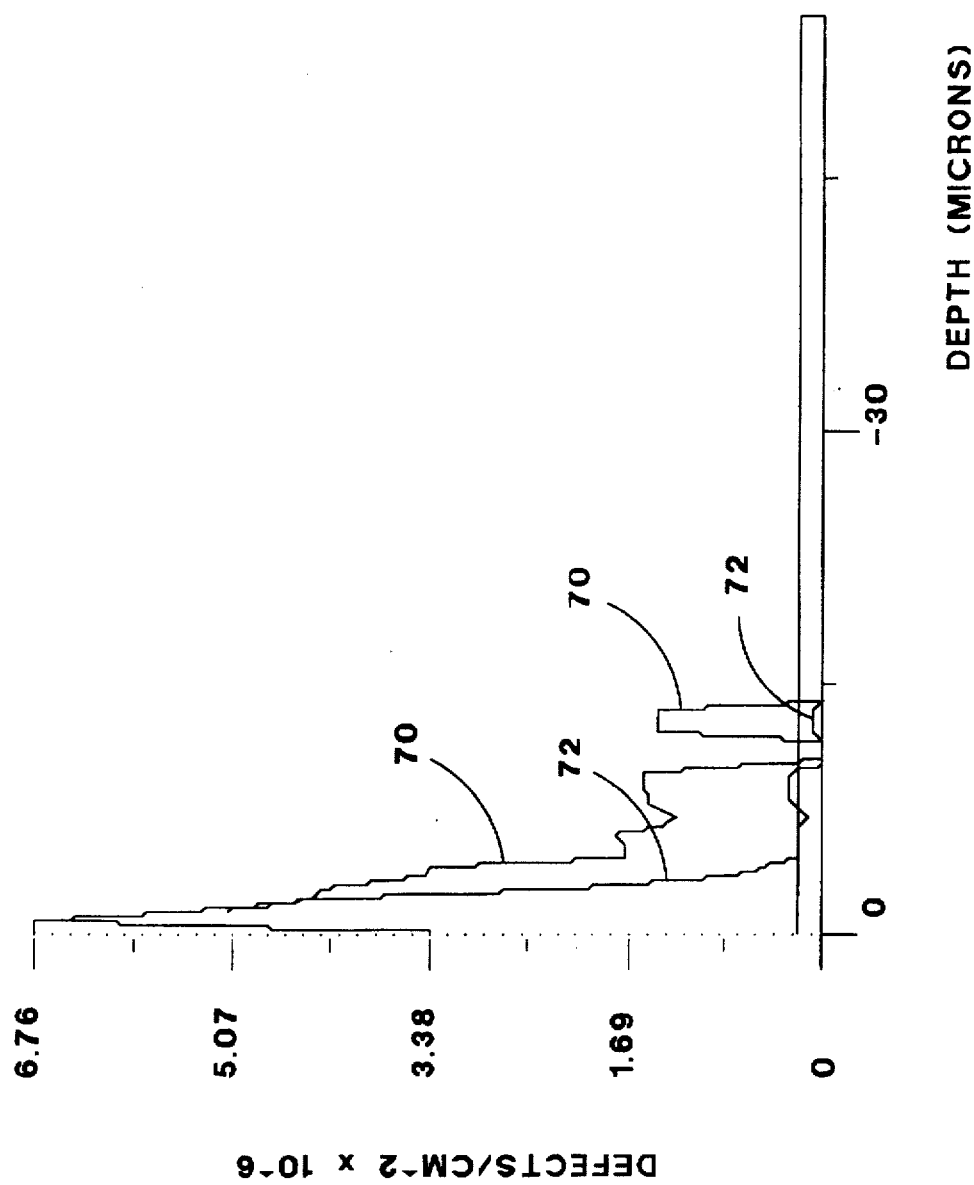
FIG. 4 is a graph comprising a defect density profile of a silicon wafer processed in accordance with the invention as measured from the back side of the wafer.

A representative wafer was selected from the batch and scanned for defects per unit area and per unit volume from its back side with an optical precipitate profiler, the resulting data being used to obtain a plot of defects/$cm^2$ in relation to depth from the back side surface, shown in FIG. 4. In the graph, 70 refers to the raw signal while 72 refers to the calculated defect density.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A method of measuring and monitoring the defect density of a wafer from its back side comprising the steps of:

(a) lapping the back side surface of said wafer;

(b) etching said back side surface of said wafer;

(c) imparting controlled damage to said back side surface of said wafer so;

(d) transmitting light from a scanner toward said back side surface of said wafer that said light reaches said back side surface prior to reaching the front side surface of said wafer; and (e) measuring the degree of scatter of said light through said wafer, thereby detecting said defect density wherein the cumulative effect of steps (a), (b) and (c) is to impart a degree of reflectivity to the back side of said wafer of from about 90% to about 100%.

2. The method of claim 1 wherein said defect density is the number of defects per unit area on said back side surface.

3. The method of claim 1 wherein said defect density is the number of defects per unit volume within said wafer.

4. The method of claim 1 wherein said etching removes from about 50 microns of material from said back side surface.

5. The method of claim 1 wherein step (c) is conducted by wet sand blasting.

6. The method of claim 1 wherein, prior to step (d), said back side surface of said wafer has a degree of reflectivity of about 90%.

7. The method of claim 1 wherein step (d) is conducted by a laser, and wherein step (e) is based upon differential interference.

8. A method of measuring the defect density of a wafer from its back side comprising the steps of:

(a) imparting a degree of reflectivity of approximately at least 90% to the back side of said wafer by performing the following substeps to the back side surface of said wafer in the following order:

(i) lapping;

(ii) etching; and (iii) abrading so as to impart controlled damage thereto;

(b) transmitting light from a scanner toward the back side surface of said wafer so that it reaches the back side surface prior to reaching the front side surface of said wafer; and (c) measuring the degree of scatter of said light through said wafer, thereby detecting defect density.

* * * * *